United States Patent [19]

Sherrod et al.

[11] Patent Number: 4,758,543

[45] Date of Patent: Jul. 19, 1988

[54] DEHYDROGENATION CATALYST

[75] Inventors: Fred A. Sherrod; Allen R. Smith, both of Lake Jackson, Tex.

[73] Assignee: The Dow Chemical Company, Midland, Mich.

[21] Appl. No.: 69,464

[22] Filed: Jul. 1, 1987

[51] Int. Cl.[4] .................. B01J 23/10; B01J 23/78; B01J 27/232

[52] U.S. Cl. ......................... 502/174; 585/444

[58] Field of Search .................. 502/174, 304; 585/444

[56] References Cited

U.S. PATENT DOCUMENTS

| | | | |
|---|---|---|---|
| 1,985,844 | 12/1934 | Sulda | 260/168 |
| 2,036,410 | 4/1936 | Graves | 260/168 |
| 2,408,140 | 9/1946 | Gutzeit | 252/230.6 |
| 2,414,585 | 1/1947 | Eggertsen et al. | 260/669 |
| 2,866,790 | 12/1958 | Pitzer | 260/290 |
| 3,223,743 | 12/1965 | MacFarlane | 260/669 |
| 3,360,579 | 12/1967 | Hills et al. | 260/669 |
| 3,364,277 | 1/1968 | Siem | 260/680 |
| 3,904,552 | 9/1975 | O'Hare | 252/458 |
| 4,098,723 | 7/1978 | Riesser | 252/474 |
| 4,144,197 | 3/1979 | Riesser | 252/462 |
| 4,460,706 | 7/1984 | Imanari et al. | 502/304 |
| 4,467,046 | 8/1984 | Smith et al. | 502/174 |

Primary Examiner—W. J. Shine
Attorney, Agent, or Firm—A. Cooper Ancona

[57] ABSTRACT

An improved dehydrogenation catalyst, useful in converting alkylaromatics to alkenylaromatics, e.g. ethylbenzene to styrene, has been discovered which contains lower amounts of iron and relatively larger amounts of cerium and potassium than those known to the art.

15 Claims, No Drawings

DEHYDROGENATION CATALYST

BACKGROUND OF THE INVENTION

This invention relates to improved catalysts for the dehydrogenation of hydrocarbons to corresponding more-unsaturated hydrocarbons, more particularly, to the production of vinyl aromatic hydrocarbons from alkyl aromatic hydrocarbons and to the production of olefins from the corresponding more saturated aliphatic hydrocarbons.

The vinyl benzenes and butadienes play a particularly important role in the preparation of synthetic rubbers, plastics and resins. The polymerization of styrene, for example, with various comonomers such as butadiene to produce synthetic rubbers is well known as is the polymerization of styrene to produce polystyrene resins.

Styrene and butadiene are typically produced from ethylbenzene and butylene, respectively, by dehydrogenation over solid catalysts in the presence of steam and at temperatures ranging from 500° C. to 800° C. The class of catalysts found to be the most effective for this process contains a predominant amount of iron oxide, promoted by potassium carbonate, and stabilized by chromium oxide. Any improvement which results in either increasing the selectivity (moles of desired product produced per mole of reactant reacted) or the conversion (moles of reactant reacted per mole of starting material) without lowering the other is economically attractive since the result is that the yield (moles of desired product produced per mole of reactant) of the product has been increased. An increase of only a few tenths of a percent in the selectivity can result in a substantial savings of starting materials while an increase in conversion can substantially reduce capital expenditure and energy consumption.

The prior art catalysts used in the dehydrogenation of alkyl aromatics to alkenyl aromatics, for example, ethylbenzene to styrene as previously discussed, are widely known. Early dehydrogenation patents describe the use of cerium oxide as the major active ingredient. Thus, for example, U.S. Pat. No. 1,985,844 discloses the use of cerium oxide precipitated on broken pieces of clay to dehydrogenate ethylbenzene below atmospheric pressure. U.S. Pat. No. 2,036,410 discloses the use of cerium oxide promoted with oxides of tungsten, uranium, and molybdenum.

Various catalysts, the dehydrogenation conditions and other operating data are disclosed by Pitzer in U.S. Pat. No. 2,866,790 relating to the use of catalyst composition including potassium carbonate, chromium oxide, and iron oxide. Other catalysts and procedures are also shown by Gutzeit, U.S. Pat. Nos. 2,408,140; Eggertsen, et al, 2,414,585; Hills, et al, 3,360,579; 3,364,277: and 4,098,723.

Belgium Pat. No. 811,145 discloses the use of cerium in promoted iron oxide dehydrogenation catalysts. Belgium Pat. No. 811,552, based on the principal patent above, discloses the use of cerium and molybdenum in potassium promoted iron oxide dehydrogenation catalysts. In these two patents iron oxide is 50-80% by weight, preferably 55-65% by weight. Cerium oxide is 0.5-10% by weight, most preferably 4-6% by weight. Potassium carbonate is present in a concentration of from 1-40% by weight.

O'Hara, in U.S. Pat. No. 3,904,552, discloses the use of cerium and molybdenum in alkali promoted iron oxide dehydrogenation catalysts. The iron oxide is employed in the catalyst at 30-90% by weight, more preferably 55-90% by weight. O'Hara's preferred alkali metal compound is potassium carbonate and is employed in amounts in the range of 1.0-40%, preferably 5-25% by weight. Cerium oxide is employed in the range of from 0.5-10% by weight, most preferably 4-6% by weight.

The use of cerium oxide in alkali promoted dehydrogenation catalysts with iron oxide percentages as low as 20% by weight has been disclosed. Thus, MacFarlane, in U.S. Pat. No. 3,223,743, teaches that it is very difficult to obtain a catalyst which has both high selectivity and high activity since, as one increases, the other usually decreases. To overcome this he teaches the use of two layers of catalyst, the first layer with high selectivity (lower activity) and a second layer with high activity (lower selectivity). The first layer with high selectivity and lower activity may contain 20-80% by weight iron and 0.5-5% by weight cerium oxide.

Riesser, in U.S. Pat. No. 4,144,197, discloses the use of vanadium to improve the selectivity of a potassium promoted dehydrogenation catalyst containing 20-95% by weight ferric oxide and 0.01-50% by weight cerium oxide. Data in this patent is consistent with the teaching of MacFarlane with respect to vanadium addition since, by increasing the amount of vanadium, the selectivity of the catalyst is increased at the sacrifice of activity. Another patent disclosing the use of oerium as a promoter in iron oxide based catalysts is U.S. Pat. No. 4,467,046.

The advantage of having a promoted dehydrogenation catalyst containing both cerium and potassium in high concentrations together with low concentrations of iron as related to the known art has not previously been recognized. Thus, catalysts containing more than 10% by weight cerium as cerium oxide and more than 40% by weight potassium as potassium carbonate and less than 30% iron as iron oxide have not been disclosed.

It has now been discovered that a highly active and highly selective dehydrogenation catalyst which contains high concentrations of both cerium and potassium compounds and small amounts of iron, but without vanadium, can be achieved using only a single catalyst layer. The catalytic components are optionally promoted with molybdenum and/or chromium compounds. From these components unitary structures are made, i.e. pellets or extrudates, by adding hydraulic cement and other binders. The catalyst pellets are then calcined before use in a dehydrogenation process.

SUMMARY OF THE INVENTION

An improved dehydrogenation catalyst useful in converting alkylaromatics to alkenylaromatics, e.g. ethylbenzene to styrene, has been discovered which contains a unique combination of relatively low amounts of iron and large amounts of cerium and potassium. Such catalysts give excellent conversions and selectivities. Catalysts in accordance with this invention contain 5-30% iron as $Fe_2O_3$, 40-60% potassium as $K_2CO_3$, and 10-60% cerium as $Ce_2O_3$ as catalytic components together with a binder. Agents, such as graphite and cellulose, can also be added to improve the porosity. These, however, burn out during the calcination process.

DETAILED DESCRIPTION OF THE INVENTION

Cerium as used in the catalyst compositions of the present invention can be added to the catalyst in the form of cerium oxide or in the form of other cerium compounds which decompose upon calcination to form cerium oxide, as for example, cerium carbonate, cerium nitrate and cerium hydroxide. The catalyst compositions of the present invention contain, by weight, from about 5 to about 30% iron as $Fe_2O_3$, preferably from about 15 to about 28%, from about 40 to about 60% potassium as $K_2CO_3$, preferably from about 45 to about 55% and from about 10 to about 60% cerium as $Ce_2O_3$, preferably from about 12% to about 30%, based on the total of the finished calcined catalyst.

The dehydrogenation catalyst compositions of the present invention contain iron as an essential catalytic component. Many forms of iron oxide are used in preparing dehydrogenation catalysts. While various forms of iron oxide can be employed in the compositions of the present invention, the preferred form employed in the catalytic compositions of the present invention is red iron oxide or a mixture of red iron oxide ($Fe_2O_3$) and yellow iron oxide ($Fe_2O_3 \cdot H_2O$). When the mixture of oxides is employed, about 30% to about 70% of the total moles of iron oxide is added as yellow iron oxide. The amount preferred is about 40-60 molar percent of the yellow oxide and the most preferred is about 50 molar percent. Particularly suited are pigment grade red and yellow iron oxides. The catalyst compositions of the invention contain from about 5% to 30% by weight, preferably from about 15% to 28%, of iron calculated as $Fe_2O_3$.

The dehydrogenation catalyst compositions of the present invention also contain as a catalyst promoter, one or more potassium compounds. The potassium promoter material can be added to the catalyst in various forms. For example, it may be added as the oxide, or as other compounds which are convertible, at least in part, under calcination conditions, to the oxide. The hydroxides, carbonates, bicarbonates, and the like are suitable. The potassium compound is preferably present in the catalyst as potassium carbonate or as a mixture thereof with potassium oxide. The present catalyst compositions comprise from about 40% to 60% by weight, and preferably from about 45% to 55% by weight, of potassium promoter compound, calculated as potassium carbonate.

Other known catalyst additives can be included in the catalysts of the invention, but are not essential. Thus, an optional component of the catalyst composition of the invention is a chromium compound which serves as a stabilizer for the active catalytic components. Chromium compounds have, in fact, typically been added to alkali-promoted iron oxide catalysts to extend their life. Chromium, as used in the compositions of this invention, can be added to the catalyst in the form of a chromium oxide or in the form of chromium compounds which decompose upon calcination to chromium oxides, as for example, chromium nitrates, hydroxides, acetates, and the like. If potassium chromates are used, such materials can, of course, also contribute to the requisite concentration of potassium essentially present in the dehydrogenation catalyst compositions as hereinbefore discussed. Catalyst compositions herein optionally contain up to about 5% by weight, preferably (when employed) from about 1% to 3%, of a chromium compound, calculated as $Cr_2O_3$.

A second optional component, used to improve the selectivity of the catalyst, is molybdenum which can be added as its oxide or as a molybdate. The molybdenum component is present (when employed) in an amount up to about 2.5% by weight, preferably about 0.2 to about 1.5% molybdenum, calculated as $MO_3$.

The physical strength, activity and selectivity of the catalyst compositions of the present invention can be improved by adding certain binding agents. Binding agents can include, for example, calcium aluminate or Portland cement. These cements can be added individually or in combination. The catalyst should contain from about 3% to about 20% by weight hydraulic cement, preferably from about 5% to about 15%. Calcium sulfate which can also be added to the composition serves to supplement the binder component and can be used to replace a portion thereof.

The density of the catalyst composition herein can likewise be modified by the addition of various filler substances, for example, combustible materials such as graphite and methyl cellulose. Such materials can be added to the compositions during preparation but are burned out after the catalyst pellets have been formed during the calcining step. These porosity promoting aids can also facilitate extrusion of catalyst pellets. These fillers generally comprise up to about 10% by weight of the catalyst composition, preferably from about 2 to about 8 percent.

The catalyst compositions of the present invention generally are prepared by admixing the essential and desired optional components heretofore described and by drying and calcining the resulting mixture. Calcination temperatures can range from about 500° C. to about 800° C., preferably from about 550° C. to 750° C. The catalyst compositions of the present invention can be prepared in various ways known to the art.

One method comprises ballmilling together a mixture of the desired compounds, adding a small amount of water, and extruding the composite to produce small pellets, which are then dried and calcined. Another method is mixing the components together with water, drying them to form a powder and tabletizing. Another procedure involves mixing the components together with an excess of water, partially drying, and then subsequently extruding, drying and calcining the resulting pellets.

The catalysts of the present invention are especially effective in promoting the dehydrogenation of ethylbenzene to produce styrene. Such a dehydrogenation reaction is usually carried out at reaction temperatures of from about 500° C. to about 700° C. However, higher or lower temperatures may be used as are known to the art. The use of subatmospheric, atmospheric, or superatmospheric pressures are suitable. However, since it is preferred to operate at as low a pressure as is feasible, atmospheric or subatmospheric pressure is preferred. The process of the invention preferably is carried out as a continuous operation. It is preferred to utilize a fixed bed which may consist of a single stage or a series of stages of the same catalyst in one or several reactors.

With the use of the catalyst of this invention, it is desirable to add steam to the hydrocarbon reactant feed to aid in the removal of carbonaceous residues from the catalyst. Steam to hydrocarbon weight ratios of from about 0.8:1 to about 5:1 are desirable depending on the compound being dehydrogenated. Best results are obtained with steam to hydrocarbon ratios above about 1:1.

The contact time of the reactant-containing gas with the catalyst is usually expressed in terms of liquid-hourly-space velocity (LHSV), which is defined as the volume of liquid hydrocarbon reactant per volume of catalyst per hour. The LHSV of the organic reactants, eg. ethylbenzene, according to this invention may vary from about 0.3 to 10 and is preferably adjusted within this range to effect the degree of conversion desired for the particular feed in question.

The catalysts of the present invention and their use will be further described by the following illustrative examples. It should be noted that advantages resulting from increases in selectivity of only a few tenths of a percent and/or increases in activity of a few degrees of temperature are extremely significant in a commercial process which may produce many hundreds of thousand pounds of product per day.

EXAMPLE 1

A catalyst according to the invention is prepared by mixing 22.0 g red $Fe_2O_3$, 198.4 g cerium oxide, 4.0 g $CaSO_4.2H_2O$, 162.6 g $K_2CO_3$, 20.4 g Portland cement, 4.1 g methyl cellulose and 39.4 g graphite with enough water to make a wet paste. The mixture is dried at 150° C., ground to a powder, and pressed into 3/16-inch tablets. The tablets are calcined at 600° C. for 1½ hours and then at 750° C. for ½ hour.

EXAMPLE 2

A catalyst is prepared according to the procedure of Example 1 except that the ratio of iron to cerium, is increased. Thus, 66.1 g $Fe_2O_3$, 154.3 g cerium oxide, 4.0 g $CaSO_4.2H_2O$, 162.6 g $K_2CO_3$, 20.4 g Portland cement, 4.1 g methyl cellulose and 39.4 graphite are used.

EXAMPLE 3

A catalyst according to the invention, using a mixture of iron oxides, is prepared, by dry blending 238.1 g cerium carbonate $[Ce_2(CO_3)_3.5H_2O]$, 120 g calcium aluminate cement (trade name LUMNITE manufactured by Lehigh Cement Co.,), 50 g graphite, 10 g methyl cellulose, 12.7 gypsum ($CaSO_4.2H_2O$), 90.9 g yellow iron oxide ($Fe_2O_3.H_2O$ which drys to 80 g $Fe_2O_3$) having a surface area below 20m²/gm and an average particle size of less than 2 microns, and 80 g red iron oxide ($Fe_2O_3$) having a surface area of about 5m²/gm and an average particle size of about 1 micron. Potassium carbonate, 500 g, is dissolved in about 500 g water and mulled with the dry-blended ingredients. After drying the mixture to a moisture content of about 10%, it is pelleted (⅛" pellets). The pellets are dried at 150° C. for about ½ hour, then calcined at 600° C. for 2-3 hours.

The weight percentage compositions of the finished calcined catalysts of Examples 1-3 are given in Table I, the balance of the total catalyst composition being the cementitious binder.

TABLE I

| Catalyst of Example | Wt. % Component | | |
|---|---|---|---|
|  | $Fe_2O_3$ | $Ce_2O_3$ | $K_2CO_3$ |
| 1 | 5.4 | 48.8 | 40.0 |
| 2 | 16.3 | 37.9 | 40.0 |
| 3 | 17.0 | 16.0 | 53.2 |

The catalysts prepared in Examples 1-3 are tested for activity and selectivity by using them in the dehydrogenation of ethylbenzene to styrene by loading the catalyst into one of two fixed bed reactors having a volume of 70 and 100 cc, respectively, and passing a preheated mixture of steam and ethylbenzene at a weight ratio of 1.0:1 or 1.5:1 into the catalyst bed, which is maintained at the temperature required to obtain the desired conversion (~50%) of ethylbenzene. The reactor pressure is maintained at essentially atmospheric. The liquid hourly space velocity (LHSV) of ethylbenzene is kept at 1.0. The effluent crude product is analyzed, the activity and selectivity to styrene are calculated and the results are shown in Table II.

TABLE II

| Catalyst of Example | Temp. °C. | Conversion | Selectivity | S/O | LHSV |
|---|---|---|---|---|---|
| 1 | 597 | 50.0 | 96.5 | 1.06 | 1 |
| 2 | 594 | 51.2 | 96.7 | 1.50 | 1 |
| 3 | 591 | 49.9 | 96.8 | 1.52 | 1 |

EXAMPLE 4

Another catalyst of the invention is prepared by dry-blending 130 g red iron oxide, 148 g yellow iron oxide, 158.7 g $Ce_2(CO_3)_3.5H_2O$ (63% cerium oxide), 120 g calcium aluminate cement (LUMNITE), 12.7 g $CaSO_4.2H_2O$, 50 g amorphous graphite, 10 g of methyl cellulose and 450 g $K_2CO_3$. Enough wateris added to these components so as to provide about 10% moisture. The mixture is then mulled and pelleted (5/32")and the pellets are calcined at a temperature of from about 550°-650° C. for about two and one half hours in flowing air. The weight percentages of this catalyst, as shown in Table III, are calculated by expressing the yellow iron oxide as $Fe_2O_3$, the cerium carbonate as $Ce_2O_3$, and the $CaSO_4.2H_2O$ as $CaSO_4$. The red iron oxide, $K_2CO_3$, and the cement are considered to remain unchanged while the graphite and methyl cellulose are considered to be burned out during the calcination step.

The catalyst is tested for activity and selectivity in the reaction for dehydrogenating ethylbenzene to styrene by placing 70 ml of the above catalyst pellets in a fixed bed reactor and passing a preheated mixture of steam and ethylbenzene at a weight ratio of 1.5:1 through the bed which is maintained at a temperature to give the desired conversion of ethylbenzene, this temperature being dependendent upon the activity of the particular catalyst. The LHSV is 1.0 and the pressure is maintained at atmospheric. The results are shown in Table III.

EXAMPLES 5-14

Other catalysts are prepared in the manner of Example 4. The cement employed is the calcium aluminate used in Example 3. Graphite and methyl cellulose are added in the same weight percentages, i.e. 5% and 1%, respectively, and the compositions are calculated and expressed as in Example 4. Pellets having the same diameter are extruded and calcined at the same temperature as in Example 4.

The compositions and results of use are shown in Table III. The activity of each catalyst is indicated by the temperature required to obtain 58% conversion of ethylbenzene. The selectivity is the percentage of converted product which is styrene.

TABLE III

| Component | \multicolumn{11}{c}{Example No. (Weight Percent)} |
|---|---|---|---|---|---|---|---|---|---|---|---|
| | 4 | 5 | 6 | 7 | 8 | 9 | 10 | 11 | 12 | 13 | 14** |
| $Fe_2O_3$* | 27.6 | 9.6 | 17.0 | 16.6 | 16.5 | 17.0 | 17.0 | 22.2 | 22.3 | 27.6 | 25.8 |
| $K_2CO_3$ | 47.9 | 47.8 | 47.8 | 46.8 | 46.4 | 58.4 | 53.1 | 47.9 | 47.8 | 47.9 | 44.6 |
| $Ce_2O_3$ | 10.5 | 21.2 | 15.9 | 15.6 | 15.5 | 10.6 | 15.9 | 12.8 | 15.9 | 10.6 | 11.9 |
| Cement | 12.8 | 18.0 | 18.0 | 17.7 | 17.5 | 12.7 | 12.8 | 12.8 | 12.7 | 12.8 | 11.9 |
| $CaSO_4$ | 1.1 | 3.2 | 1.1 | 3.1 | 3.1 | 1.1 | 1.1 | 3.2 | 1.1 | 1.1 | 1.6 |
| $MoO_3$ $Cr_2O_3$ | 0.0 | 0.2 | 0.2 | 0.2 | 1.0 | 0.2 | 0.2 | 1.1 | 0.2 | 0.2 | 1.0 |
| T(°C.) at 58% conv. | 605 | 598 | 605 | 598 | 600 | 608 | 602 | 598 | 597 | 602 | 595 |
| % Selectivity | 95.8 | 95.5 | 96.0 | 96.3 | 95.7 | 96.2 | 95.9 | 95.8 | 96.1 | 95.9 | 95.8 |

*The iron oxide is a mixture of the yellow and red oxides, 50% of the $Fe_2O_3$ being obtained from each.
**In this catalyst preparation only 2% graphite is employed and $Cr_2O_3$ is added as $K_2Cr_2O_7$.

COMPARATIVE EXAMPLE

A preferred catalyst of the prior art (Example 1, U.S. Pat. No. 3,904,552) is prepared by the same procedure used to produce catalysts of the present invention. The following components are thoroughly mixed with water to a suitable consistency for extrusion.

| Components | Parts by Weight |
|---|---|
| $Fe_2O_3$ | 600 |
| $K_2CO_3$ | 210 |
| Portland Cement | 115 |
| $MoO_3$ | 25 |
| $Ce_2(CO_3)_3 \cdot 5H_2O$ | 79.4 |

The paste is extruded to form pellets having 5/32-inch diameter. The pellets are calcined in air at 550°–650° C. for about three hours (ramped temperature). The components added are equivalent to 60% $Fe_2O_3$, 21% $K_2CO_3$, 11.5% Portland cement, 2.5% $MoO_3$, and 5.0% $Ce_2O_3$.

A temperature of 601° C. is required to give 50% ethylbenzene conversion at a steam/oil ratio of 1.5 and an LHSV of 1.0. A selectivity to styrene of 95.7% is achieved under these conditions. By comparison catalysts of the present invention (average of Examples 4–14, inclusive) produce a conversion of 58% at the same temperature with no loss in selectivity.

We claim:

1. A dehydrogenation catalyst composition which comprises a cement binder together with catalyst components of cerium as $Ce_2O_3$, potassium as $K_2CO_3$ and iron as $Fe_2O_3$ in amounts of from about 10 to about 60%, from about 40 to about 60% and from about 5 to about 30%, respectively, all by weight in the finished catalyst.

2. The composition of claim 1 wherein the amounts of cerium, potassium and iron are from about 12 to about 30%, about 45 to about 55% and about 15 to about 28%, respectively.

3. The composition of claim 1 wherein the cement binder is present in an amount of from about 3 to about 20 percent by weight of the total composition.

4. The composition of claim 2 wherein the cement binder is present in an amount of from about 5 to about 15 percent by weight of the total composition.

5. The composition of claim 1 wherein the cement binder is Portland cement.

6. The composition of claim 1 wherein the cement binder is a calcium aluminate cement.

7. The composition of claim 5 wherein the cement binder is present in an amount of from about 3 to about 20 percent by weight of the total composition.

8. The composition of claim 6 wherein the cement binder is present in an amount of from about 3 to about 20 percent by weight of the total composition.

9. The composition of claim 7 wherein a portion of the cement binder is replaced by $CaSO_4$.

10. The composition of claim 8 wherein a portion of the cement binder is replaced by $CaSO_4$.

11. The composition of claim 1 wherein the catalyst contains chromium or molybdenum promoters or a mixture thereof.

12. The composition of claim 11 wherein the chromium promoter is present in an amount of up to about 5 percent, calculated as $Cr_2O_3$.

13. The composition of claim 11 wherein the molybdenum is present in an amount of up to about 2.5 percent, calculated as $MoO_3$.

14. The composition of claim 2 wherein a chromium promoter is present in an amount of about 1 to about 3 percent by weight, as $Cr_2O_3$.

15. The composition of claim 2 wherein a molybdenum promoter is present in an amount of from about 0.2 to about 1.5 percent by weight, as $MoO_3$.

* * * * *